United States Patent [19]

Freedman

[11] Patent Number: 4,989,968
[45] Date of Patent: Feb. 5, 1991

[54] PHOTOSCREENING CAMERA SYSTEM

[76] Inventor: Howard L. Freedman, 3113 E. Lake Sammamish Pkwy., NE., Redmond, Wash.

[21] Appl. No.: 387,697

[22] Filed: Jul. 31, 1989

[51] Int. Cl.$^5$ .............................................. A61B 3/14
[52] U.S. Cl. .................................... 351/206; 351/208
[58] Field of Search ................ 351/206, 205, 221, 208

[56] References Cited

U.S. PATENT DOCUMENTS 4,717,952 1/1988 Kohayakawa et al. ............. 351/206

Primary Examiner—Paul M. Dzierzynski
Attorney, Agent, or Firm—Kane, Dalsimer, Sullivan, Kurucz, Levy, Eisele and Richard

[57] ABSTRACT

The present invention relates to a camera system for detecting photorefractive errors in a patient's eyes and for detection of ocular misalignment, media opacities and other abnormalities of the eyes and the lids. The invention includes a strobe mounted adjacent to a lens shield to create a slit aperture and which flash is rotated 90 degrees for vertical and horizontal or oblique photographs of different meridians. The camera has either a plurality of a mirrors forming a foldable light path or a telescopic or telephoto lens and a shorter light path to provide magnification of the image for one to one imaging.

27 Claims, 3 Drawing Sheets

PHOTOSCREENING CAMERA SYSTEM

BACKGROUND OF THE INVENTION

The present invention relates to a photoscreening camera system. In particular the present invention relates to a method and an apparatus for detecting the photorefractive error of a patient's eye for diagnosing amblyopia and for detecting misalignment of the eyes (strabismus) and opacities in ocular media and other observable ocular abnormalities.

The principles behind photorefraction is covered in an article entitled "Quantitative Photorefraction Using An Off-Center Flash" *Physiologic Optics*, 1989, Vol. 65, pp. 962-971. The underlying principal of photoscreening is that by taking a special photographic picture of a child's eye, the factors which can lead to amblyopia (or lazy eye) can be detected. These three main factors are unequal refractive errors, misalignment of the eyes, and opacities in the ocular media such as cataracts. One can also detect asymmetry of the lids, asymmetry of the pupils, and any external abnormalities around the eye in the photograph.

The prior art literature on eccentric flash photoscreening systems describes either one- or two-flash systems. A two-flash system is described in U.S. Pat. No. 4,523,820 to Kaakinen. The Kaakinen patent covers only two flashes used simultaneously or one flash with two objectives. His patent does not cover one-flash systems, even when one flash is used to check one meridian and then that one flash is rotated to another meridian. U.S. Pat. No. 4,669,836 to Richardson covers a one-flash camera system using an LED for FIXATION control as well as a very elaborate structure to hold the child's head rigid. The test distance of this system is 2.4 meters and it utilizes the long distance from the subject to the camera to achieve measured sensitivity. The eccentricity of the flash with respect to the objective of the camera is large, with the flash being placed outside of the objective of the camera. The flash does not rotate and one can only measure one meridian of abnormalities. The camera system is therefore insensitive to the detection of astigmatism and small degrees of refractive error, and it is not fully portable nor hand-held. It also does not utilize instant film for ease and rapidity of interpretation.

U.S. Pat. No. 4,586,796 to Molteno utilizes a ring flash which is placed very close to the edge of the camera objective. A full ring flash is not disclosed in the Kaakinen patent. The same optical principles apply in all eccentric photorefraction, but note that the eccentricity in the Molteno device is larger because its flash is significantly farther away from the center of the objective or the edge of the lens aperture compared to present invention and therefore the sensitivity of that camera system is less.

The description of the optics of the photorefraction are described by Dr. Howard Howland in an article entitled "Optics of Photoretinoscopy: Results from Ray Tracing", *American Journal of Optometry and Physiologic Optics*, Vol. 62, pp. 621-625, 1985. The article describes isotropic photorefraction with the light flash right in the center of the lens objective. It discloses a flash unit which is placed centrally in the optical axis of the system and creates an eccentric aperture by creating a shield below and around the optical flash. This system does not have a central lens aperture (a slit) nor use an eccentric flash.

However, by utilizing the formula (disclosed in the article) for determining the optimal sensitivity of the camera and dioptric thresholds, one can obtain a sensitivity, based upon an eccentricity of the flash edge from the edge of the lens aperture of about 1 mm, which is significantly better than even the best system (which was previously described as the Molteno system), with a 0.09 diopter sensitivity with an 5 mm pupil.

The article "Eccentric Photorefraction: Optical Analysis and Empirical Measures" by Bobier and Braddick, *American Journal of Optometry, and Physiologic Optics*, Vol. 62, pp. 614-620, 1985, describes an analysis of the optics of eccentric photorefraction. The article describes eccentricity as the distance above the extreme edge of the camera lens and describes the eccentricity of the flash source beyond the margin of the lens aperture. The theoretical curves of best sensitivity which are obtained are different from the theoretical curves of the present invention due to the present invention's minimal eccentricity of the flash from the edge of the aperture lens which permits a null interval of nearly zero (0.0250). Using this formula, the minimal defocus of the eye which one can detect is 0.10 diopters with a 10 mm pupil, which agrees with the findings and the sensitivity of the camera of the present invention. The minimal eccentricity is obtained by using ASA 3000 black and white film or other high sensitivity imaging films and a narrow aperture and flash eccentricity. Also by proper rotation of the flash source, one can have the effective output of the flash at the edge of the strobe, further increasing the sensitivity of the camera system.

Accordingly, it would be desirable to create a slit aperture with a minimal eccentricity approximately 1 mm by placing the strobe edge as the edge of the lens aperture while using a high ASA film or a light sensitive video camera detection system or other imaging device.

It is desirable to use a high speed (black and white) film e.g. (ASA 3000) to create a small aperture and eccentricity, since with using a slower ASA e.g. (ASA 600) color film, the minimum aperture would be 5-6 mm (rather than the 3 mm aperture which can be utilized with black and white film) to have enough light enter the aperture of the camera for proper exposure.

It is also desirable to provide for a photoscreening camera for detecting misalignment of the eyes by evaluating the corneal reflection caused by the appearance of the flash on the eye similar to the Hirschberg test used in clinical practice and by detecting an intensity difference of the red reflex, which is seen as a brighter image in a misaligned eye, so described as the BRUCHNER reflex. Thus, a brightness difference of the red reflex of the eyes can indicate misalignment of the eye even when the corneal reflection appears to be symmetrical. Brightness differences can show misalignment of greater than 2°-3°.

SUMMARY OF THE INVENTION

It is therefore desirable to provide a method and an apparatus which avoid the aforementioned drawbacks of the prior art proposals in which either a camera or a high intensity video camera has a small eccentricity and aperture and utilizes high speed film to detect for refractive error, strabismus, alignment, cataracts and media opacities of a patient's eye. The invention relates to a band of light or flash which can be rotated. In particular, the band of light exits the camera adjacent to the lens aperture and has a special arrangement so that the light from the flash tube does not expose the film. In addition, the camera has a narrow aperture such as a slit aperture that rotates.

The invention further includes a strobe, such as a Polaroid flash, tilted 24 degrees to use the parabola in back of the flash and to place the effective output of the flash at its edge. The invention uses the strobe edge as the lens aperture to reduce the eccentricity to close to zero to maximize testing sensitivity. Further improvements include rotating the strobe to photograph in the vertical, oblique and horizontal directions along different meridians, a parallax alignment and focusing system in which two light images are projected onto the patient's face and the proper distance and height is obtained by moving and aligning the light images until they touch each other. The camera further has a plurality of mirrors forming a foldable light path to provide a long focal distance for increased magnification of the image or in the alternative a telescopic or a telephoto lens system and a shorter light path can be used. As used herein the term "telescopic" shall mean both a conventional telephoto lens or a telescopic lens system.

DETAILED DESCRIPTION OF THE PREFERRED EMBODIMENTS

Figure 1:
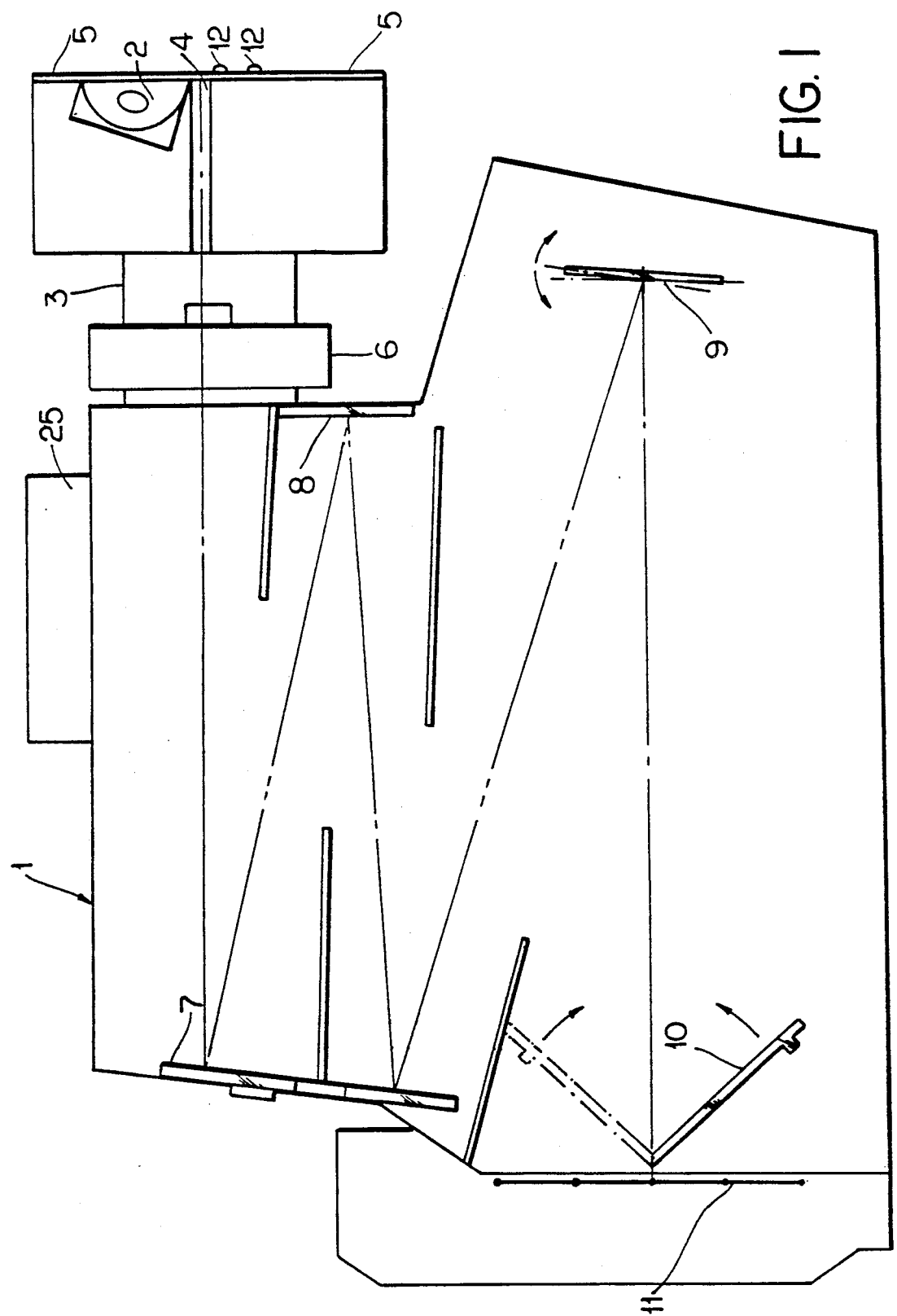
FIG. 1 shows a four mirror foldable light path system in accordance with the teachings of the present invention.
Figure 2:
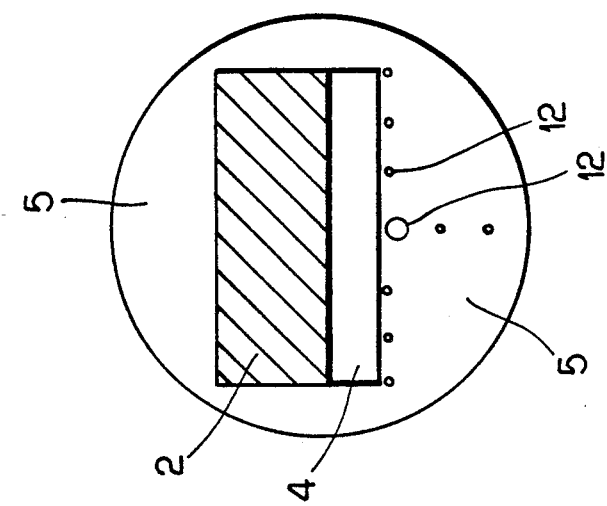
FIG. 2 shows a front view of the strobe/shield arrangement of the present invention.

Referring now to FIGS. 1 and 2, the present invention relates to a camera 1 having a strobe 2 and a lens 3 disposed behind the strobe 2.

The lens 3 is located behind a narrow aperture 4, preferably shaped as a slit aperture, on one side of which is the strobe 2 that provides the flash. On the opposite side of the aperture 4 is a shield 5.

It is important that the flash be aligned as close as possible to the edge of the lens aperture and the center of the optical axis to permit detection of a red retinal reflection and to maximize the sensitivity of the system, and, by proper positioning of the flash, one can detect and analyze the light exiting from the eye which has been defocussed by the refractive error of the eye, and by analyzing the size and appearance of these white crescents within the red reflex determine, on a relative basis, the size and type of the refractive error. Thus, as described below, in accordance with the present invention the flash is positioned to define the edge of the lens aperture. Asymmetry of crescent size or defocus indicates anisometropia, meaning unequal refractive errors, which can lead to amblyopia.

A shutter 6 is positioned behind the strobe 2 and the aperture 4. The shutter 6 is wide open but can be made smaller to improve light exposure. The open aperture arrangement of the shutter 6 does not affect the exposed film 11 in the camera 1, rather it is the distance between the flash and the slit 4 that creates the effective aperture of the camera and thus minimizes the lens/flash eccentricity of the camera 1 by placing the flash very close to the outer edge of the camera aperture (the slit 4). The slit 4 is preferably 3 mm wide.

A parallax aiming system 25 is another feature of present invention. Two light images are projected onto the forehead of the patient and when the camera distance is adjusted and the lights touch each other the proper focusing distance and alignment are obtained. Alternatively the parallax aiming system can consist of any system in which the two lights, which can be of different colors sizes or shapes, move back and forth, without necessarily touching, until proper focus, proper height and aiming alignment is achieved.

The strobe 2 can be rotated in both the vertical, oblique and horizontal directions to permit photographing different meridians of refractive error. The camera 1 uses ASA 3000 black and white film but can use any front surface or back surface exposure film or video recording device.

Two exposures are taken and placed on one sheet of film, one exposure is taken when the strobe 2 is rotated vertically and the other exposure is taken when the strobe or camera is rotated horizontally or in other oblique directions approximately 90° apart.

The strobe 2 is tilted to place effective flash output at the edge of the strobe to minimize the eccentricity and to maximize sensitivity. The angled strobe 2 is rotated 90 degrees about the optical center line in order to take the vertical and horizontal or oblique pictures.

The camera 1 has three mirrors 7, 8, 9 forming a 4 reflection foldable light path thereon. Mirror 7 accomplishes two reflections. One mirror 9 is rotatable and two mirrors 7 and 8 are fixed. The last mirror 9 in the foldable light path is rotatable and is an image spitter as it serves to place two images on one sheet of film. By rotating mirror 9 a few degrees the image can be moved to either the superior or inferior half of the film. Thus, the two exposures, discussed above, can be produced on one sheet of film. By thus, incorporating two pictures on one sheet of film, film costs are reduced. A rotating shield 10 is placed in front of the film 11 to shield the other half of the film from inadvertent light exposure. Light travels through the camera 1 and through the folded light path formed by the three mirrors 7, 8 and 9 therein. The folded light path provides for a very large focal distance thus providing a large magnification of the image resulting in an approximate one to one image size.

Figure 3:
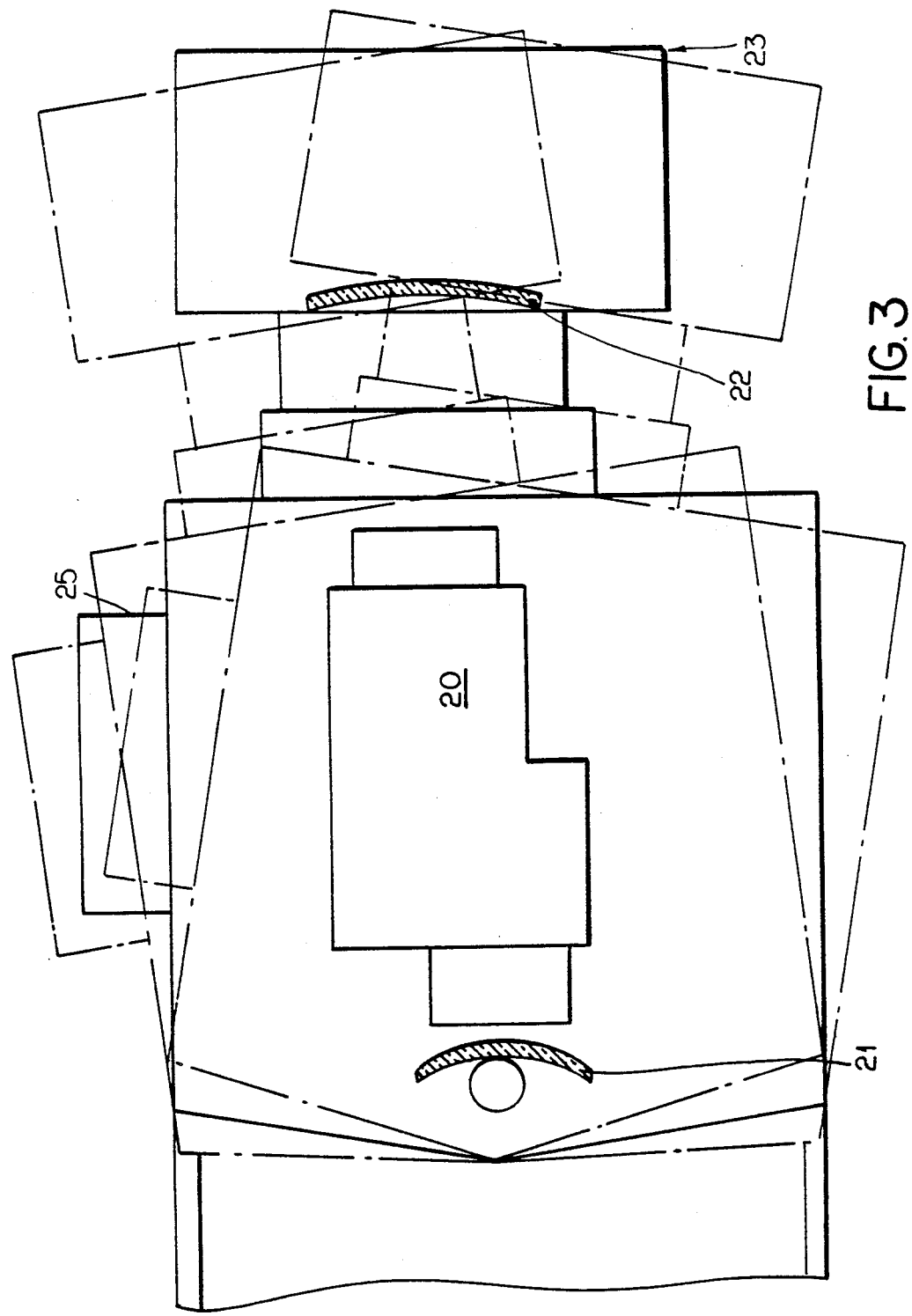
FIG. 3 shows an alternate embodiment in which a telescopic lens system is utilized in accordance with the present invention.

Alternatively, as shown in FIG. 3, a telescopic lens system can be utilized with a shorter light path to create the magnification of the image. The telescopic lens system of FIG. 3 would preferably have a monocular telescope 20 which magnifies the image. An imaging lens 21 focuses the magnified image onto film such as instant film that is exposed from its rear surface e.g. Polaroid black and white film. In addition, as shown in FIG. 3, a projection lens 22 is provided at the front part 23 of the camera to project to infinity from the viewpoint of the telescope. The front part 23 of the camera would pivot as shown in FIG. 3 to direct the image to the upper and lower parts of the film. The rotary shield functions in the same fashion as described with regard to FIG. 1 to shield the part of the film not receiving an image. The front part 23 of the camera is also capable of up and down translational movement to move the image relative to the film.

A flashing light emitting diode (LED) or series of LEDS 12, which can be red or any other color, are placed just below the slit 4 in the shield 5, to attract the fixation of the child (patient) to the center of the lens to ensure maximum sensitivity and reliability of accommodation and alignment.

A sound generator (not shown) can also be incorporated into the camera system 1 to attract the child's attention.

A Polaroid auto film back is placed at the focal distance of the camera and by means of a special chip and circuit board ejects the film automatically after the two exposures.

Alternatively, manual ejection of the film can be employed depending on the preference of the user. Film expulsion can be delayed until a button is pushed rather than using the chip and circuit board.

Further, the 1:1 magnification can be achieved by utilizing other methodology such as a telescopic lens or other magnifying system rather than the foldable mirror path.

Alternatively, it is possible to use a high intensity video camera or other imaging systems to detect the light rays for analysis.

In another embodiment of the present invention, a three mirror, three reflection foldable light path is used and color or front exposure film is used with a flash.

The camera 1 preferably further includes an interlock mechanism that prevents the film from being ejected until the vertical, horizontal or oblique pictures are recorded on the same sheet of film.

The camera 1 further includes handles for portability and for holding the camera at chest or eye height.

Obviously numerous modifications can be made to the invention without departing from its scope as defined in the appended claims.

What is claimed is:

1. A camera for detecting the photorefractive errors as well as strabismus, media opacities and ocular abnormalities of a patient's eyes for the purpose of diagnosing factors which can lead to amblyopia, comprising:
   a strobe for providing a flash of light to a patient's eyes and having a strobe edge;
   a lens disposed behind said strobe, said lens including a shutter and a narrow aperture defined on one side by said strobe edge to minimize the eccentricity of the flash with respect to the lens aperture;
   a plurality of mirrors inside of said camera's housing forming a foldable light path to receive and reflect light reflected back from the patient's eyes to provide a long focal length and a large magnified image indicating any photorefractive error or strabismus, media opacities or other ocular abnormalities of the patient's eyes which are detectable including differences in brightness of the red reflex, abnormalities in corneal light reflection, appearance of opacities in the red reflex, and photorefractive errors causing defocus of light exiting the eye imaged by the camera.

2. A camera according to claim 1 further comprising means for rotating said aperture in a horizontal direction and in a vertical direction or oblique directions in order to photograph different meridians or refractive error.

3. A camera according to claim 1 wherein said camera utilizes a high speed black and white film.

4. A camera according to claim 1 further comprising a single or a series of flashing light emitting diodes disposed immediately at or below said aperture for obtaining the patient's fixation at the center of the lens for maximum sensitivity and reliability of testing.

5. A camera according to claim 1 further comprising a sound generator for attracting the patient's attention.

6. A camera according to claim 1 wherein said strobe has an effective output at its edge.

7. A camera according to claim 1 further comprising handles attached to said camera to permit said camera to be portable and to be held at chest or eye height and a parallax aiming system in which the camera or lights are moved back and forth until the proper focus, height and aiming alignment are achieved.

8. A camera according to claim 1 wherein said camera is a high intensity and sensitivity video camera.

9. A camera according to claim 1 wherein said camera is a recording image means capable of recording two meridians photographed at separate times.

10. A camera according to claim 1 wherein said camera is rotatable and said flash is set at a certain position in order to photograph different meridians.

11. A camera according to claim 1 wherein said aperture is a slit aperture.

12. A camera for detecting the photorefractive errors as well as strabismus, media opacities and ocular abnormalities of a patient's eyes for the purpose of diagnosing factors which can lead to amblyopia, comprising:
   a strobe for providing a flash of light to a patient's eyes and having a strobe edge;
   a lens disposed behind said strobe, said lens including a shutter and a narrow aperture defined on one side by said strobe edge to minimize the eccentricity of the flash with respect to the lens aperture;
   a plurality of mirrors inside of said camera's housing forming a foldable light path to receive and reflect light reflected back from the patient's eyes to provide a large magnified image containing any photorefractive error or strabismus, media opacities or other ocular abnormalities of the patient's eyes which are detectable including differences in brightness of the red reflex, abnormalities in corneal light reflection, appearance of opacities in the red reflex, and photorefractive errors causing defocus of light exiting the eye imaged by the camera;
   wherein said narrow aperture is rotatable and includes a shield behind which is located said shutter which is wide open so that said strobe and said shield form said aperture thereby creating an effective lens aperture to minimize the eccentricity of the flash and to maintain the flash close to the edge of the lens aperture.

13. A camera for detecting the photorefractive errors as well as strabismus, media opacities and ocular abnormalities of a patient's eyes for the purpose of diagnosing factors which can lead to amblyopia, comprising:
   a strobe for providing a flash of light to a patient's eyes and having a strobe edge;
   a lens disposed behind said strobe, said lens including a shutter and a narrow aperture defined on one side by said strobe edge to minimize the eccentricity of the flash with respect to the lens aperture;
   a plurality of mirrors inside of said camera's housing forming a foldable light path to receive and reflect light reflected back from the patient's eyes to provide a large magnified image containing any photorefractive error or strabismus, media opacities or other ocular abnormalities of the patient's eyes which are detectable including differences in brightness of the red reflex, abnormalities in corneal light reflection, appearance of opacities in the red reflex, and photorefractive errors causing defocus of light exiting the eye imaged by the camera;
wherein said camera utilizes front or back surface imaging instant film and said plurality of mirrors includes three mirrors and an odd number of light reflections forming said foldable light path within said camera.

14. A camera for detecting the photorefractive errors as well as strabismus, media opacities and ocular abnormalities of a patient's eyes for the purpose of diagnosing factors which can lead to amblyopia, comprising:
a strobe for providing a flash of light to a patient's eyes and having a strobe edge;
a lens disposed behind said strobe, said lens including a shutter and a narrow aperture defined on one side by said strobe edge to minimize the eccentricity of the flash with respect to the lens aperture;
a plurality of mirrors inside of said camera's housing forming a foldable light path to receive and reflect light reflected back from the patient's eyes to provide a large magnified image containing any photorefractive error or strabismus, media opacities or other ocular abnormalities of the patient's eyes which are detectable including differences in brightness of the red reflex, abnormalities in corneal light reflection, appearance of opacities in the red reflex, and photorefractive errors causing defocus of light exiting the eye imaged by the camera;
wherein said camera utilizes high speed instant ASA 3000 black and white film and said plurality of mirrors includes four mirrors with an even number of light reflections and a series of baffles forming said foldable light path within said camera.

15. A camera according to claim 14 further comprising means for rotating the last mirror in said foldable light path a few degrees to move the received image into either a first half or a second half of a film thereby incorporating two pictures on one sheet of film.

16. A camera according to claim 14 further comprising means for taking separate pictures to test different meridians.

17. A camera according to claim 14 further comprising means for rotating the camera to test different meridians.

18. A camera according to claim 15 further comprising a rotating shield placed in front of the film plane to shield the other half of the film from inadvertent light exposure.

19. A camera according to claim 18 further comprising means for ejecting the film after two exposures.

20. A camera according to claim 19 wherein said means for ejecting further comprises an electronic circuit board within said camera, and an automatic film back placed at the focal distance of said camera for automatically ejecting the film after two exposures.

21. A camera according to claim 19 wherein said means for ejecting comprises manual means for ejecting said film.

22. A camera for detecting the photorefractive errors as well as strabismus, media opacities and ocular abnormalities of a patient's eyes for the purpose of diagnosing factors which can lead to amblyopia, comprising:
a strobe for providing a flash of light to a patient's eyes and having a strobe edge;
rotating means for rotating said strobe substantially 90 degrees about the optical center line in order to take vertical, horizontal or oblique pictures;
an interlock mechanism to prevent film from being ejected until the vertical, horizontal or oblique pictures are recorded on the same film;
a lens disposed behind said strobe, said lens including a shutter and a narrow aperture defined on one side by said strobe edge to minimize the eccentricity of the flash with respect to the lens aperture;
a plurality of mirrors inside of said camera's housing forming a foldable light path to receive and reflect light reflected back from the patient's eyes to provide a large magnified image containing any photorefractive error or strabismus, media opacities or other ocular abnormalities of the patient's eyes which are detectable including differences in brightness of the red reflex, abnormalities in corneal light reflection, appearance of opacities in the red reflex, and photorefractive errors causing defocus of light exiting the eye imaged by the camera.

23. A method for detecting the photorefractive error of a patient's eyes, comprising:
photographing different meridians of refractive error by means of a strobe that provides a flash of light to a patient's eyes and a rotating device for rotating said strobe 90 degrees about the optical center line to photograph along horizontal, vertical and oblique directions;
minimizing the eccentricity of the flash from lens aperture by means of a narrow aperture formed by the proximity of the edge of the flash to a shield and a lens disposed behind said strobe and said lens including a shutter, said strobe being placed close but eccentric to the edge of said narrow aperture; and
said camera having a long focal length in a short housing, said focal length providing a large magnified image by means of a plurality of mirrors inside the camera's housing forming a foldable light path to receive and reflect light reflected back from the patient's eyes and face.

24. A method according to claim 23 wherein said narrow aperture is shaped as a slit.

25. A method according to claim 23 wherein said strobe has an effective output at its edge.

26. A camera for detecting the photorefractive errors as well as strabismus, media opacities and ocular abnormalities of a patient's eyes for the purposes of diagnosing factors which can lead to amblyopia, comprising:
a strobe for providing a flash of light to a patient's eyes and having a strobe edge;
a lens disposed behind said strobe, said lens including a shutter and a narrow aperture defined on one side by said strobe edge to minimize the eccentricity of the flash with respect to the lens aperture; and
a telescopic lens to receive light reflected back from the patient's eye to provide a long focal length and a large magnified image indicating any photorefractive error or strabismus, media opacities or other ocular abnormalities of the patient's eyes which are detectable including differences in brightness of the red reflex, abnormalities in corneal light reflection or appearance of opacities in the red reflex, and photorefractive errors causing defocus of light exiting the eye imaged by the cornea.

27. A camera according to claim 26 wherein said aperture is a slit aperture.

* * * * *